(12) United States Patent
Graham et al.

(10) Patent No.: US 9,518,984 B2
(45) Date of Patent: Dec. 13, 2016

(54) SEPARATION, WASHING AND DETERMINATION OF ANALYTES TAGGED WITH MAGNETIC PARTICLES

(75) Inventors: Henry A. Graham, Solana Beach, CA (US); John G. Gorman, Del Mar, CA (US); James P. Rowell, Stockton, NJ (US)

(73) Assignee: CHROME RED TECHNOLOGIES, LLC, Stockton, NJ (US)

( * ) Notice: Subject to any disclaimer, the term of this patent is extended or adjusted under 35 U.S.C. 154(b) by 1063 days.

(21) Appl. No.: 13/385,427

(22) Filed: Feb. 21, 2012

(65) Prior Publication Data

US 2012/0214175 A1     Aug. 23, 2012

Related U.S. Application Data

(60) Provisional application No. 61/463,735, filed on Feb. 22, 2011.

(51) Int. Cl.
*G01N 33/543*     (2006.01)
*G01N 33/80*     (2006.01)

(52) U.S. Cl.
CPC ........ *G01N 33/54326* (2013.01); *G01N 33/80* (2013.01); *G01N 2446/00* (2013.01)

(58) Field of Classification Search
CPC .............. G01N 33/54326; G01N 33/80; G01N 2446/00

USPC .......................................................... 436/526
See application file for complete search history.

(56) References Cited

U.S. PATENT DOCUMENTS

| | | | |
|---|---|---|---|
| 6,180,418 B1 * | 1/2001 | Lee ...................... | C12Q 1/6816 435/6.16 |
| 2006/0205093 A1 * | 9/2006 | Prins ............................. | 436/526 |
| 2007/0172890 A1 * | 7/2007 | Prins et al. .................... | 435/7.1 |
| 2007/0172899 A1 * | 7/2007 | Graham et al. ............... | 435/7.21 |

* cited by examiner

*Primary Examiner* — Mark Shibuya
*Assistant Examiner* — Pensee Do
(74) *Attorney, Agent, or Firm* — Ralph T. Lilore

(57) ABSTRACT

Method for detecting a material of interest, usually an antibody or an antigen on a red blood cell, in a liquid, by observing the potential antigen/antibody reaction products in a novel way. Reaction products are deposited on a magnetic substrate and will exhibit different properties depending upon whether or not the antigen/antibody reaction has taken place. An antigen/antibody reaction product adheres tenaciously to itself and the substrate while the deposit of any unreacted magnetically tagged material is weakly adhering and easily disrupted and dislodged under a disruptive force which would be insufficient to dislodge the reacted deposit. This difference in cohesive property provides the means by which a positive result is distinguished from a negative result.

20 Claims, No Drawings

US 9,518,984 B2

SEPARATION, WASHING AND DETERMINATION OF ANALYTES TAGGED WITH MAGNETIC PARTICLES

CROSS REFERENCE TO RELATED APPLICATIONS

This Application claims the benefit of U.S. Provisional Application Ser. No. 61/463,735 entitled, Separation, Washing and Determination of Analytes Tagged with Magnetic Particles, filed Feb. 22, 2011.

STATEMENT REGARDING FEDERALLY SPONSORED RESEARCH OR DEVELOPMENT (Not Applicable)

REFERENCE TO A SEQUENCE LISTING, A TABLE, OR A COMPUTER PROGRAM LISTING APPENDIX SUBMITTED ON COMPACT DISC (SEE 37 CFR 1.52(e)(5))

(Not Applicable)

BACKGROUND OF THE INVENTION

Field of the Invention

This invention relates to a novel method and novel device for separating and washing cells, particles, and molecules or analytes, unreacted reagents, and other materials of interest (MOI) from associated or contaminating material or unwanted material such as proteins, for use in many procedures such as assays, diagnostic procedures, and preparative processes.

It relates primarily to determination of antigens, antibodies and other proteins on blood cells, in blood serum and other bodily samples and the use of buffers and other liquids in the determination process wherein magnetic propulsion of magnetic particles through a clean wash fluid and onto a capture device is effected.

The invention further relates to blood banking immunological diagnostic testing and immunohematology and more particularly to blood cell serological testing using magnetic particles and magnets to separate bound entities to be measured from unbound entities.

More particularly still, the invention relates to the separation and washing of materials as aforesaid in conjunction with the determination of the presence or absence of a MOI in which red blood cells are used in the assay system through the use of magnetic forces to move relevant materials through a clean wash fluid zone thereby to effect a washing of the relevant materials, and into a novel capture device in which a capture agent is present.

The invention relates to blood bank assay systems, and with some modification also is applicable to cell separations and microscopy, immunoassays, genetic testing and molecular separations as well as many other scientific procedures and quality control processes, wherein magnetic particles and magnetic forces are used to effect the separation in a liquid medium.

Finally, it relates to performing the above procedures by utilizing magnetic forces on reactive magnetic particles and test liquids containing materials of interest.

Description of Related Art

Clinical and industrial laboratories and chemical manufacturing plants represent an enormous, widespread industry in which many procedures and processes require, or are significantly enhanced by separation of a known or unknown material of interest from materials in the process which are not of interest, and which may interfere with suitable performance of the procedure or processes.

Many of these procedures are assays performed to determine the presence or absence of the amount of a given entity in a sample which is present, along with many other entities. In the health and medical sectors, this includes, for example, the isolation, expansion and identification of genetic material, usually from body liquids or tissues, as well as the detection and quantification of antigens, antibodies, and other proteins and small molecules. On the environmental level, it is desirable to determine the amount or presence of materials in water, air, chemicals, foods and the like.

Modern-day immunoassays are a good example of the many and varied laboratory and manufacturing procedures and processes that require purification of a material by washing and separation from contaminants and other materials. Immunoassays in which small amounts of an analyte are sought and measured in a sample, have evolved from the early, generally chemical, formats of various kinds of techniques. Binding partners, either specific for a given epitope or polyclonal in nature, have been employed in reaction with the desired target (be it known or unknown) to produce an entity which can be detected through a label attached to it or through some discernable, measurable effect upon a component of the test or on a substrate reactable with the label. Generally speaking, most, of the commercially useful versions of such tests require that the reacted binding partner be separated from unreacted binding partner so as to determine whether the sought entity has reacted or not reacted and how much is present.

The need to separate reactants from interfering substances is a major design feature in immunoassays, blood bank procedures, and chemical synthesis procedures. Many variations on several separation or washing techniques have been utilized, often involving dilution with large quantities of wash solution or sample, and often presenting the element of the test which determines the ease, complexity, cost, overall time, and sensitivity of the test, as well as the design of automated assay systems and the volume of hazardous material to be controlled and discarded. Immunoassays typically use both dilution and decanting or lateral liquid flow on chromatographic membrane or paper strip or other flow-through device, with large quantities of diluent or sample as washing methods. If a convenient separation method could be made available, alternative methods would be more readily adopted. An appropriate alternative separation concept would be broadly useful for immunoassays, including the special case of immunoassays that are utilized in blood banking involving cellular antigens and antibodies to them, and sequential chemical synthetic procedures.

Historically, a very common wash method in immunoassays involves the immobilization of a reagent antibody on a portion of the surface of individually coated containers, such as a microtiter well or test tube, then washing away undesired material by repeated wash solution additions and decanting steps. When this method is used, the final reaction is observed in the same tube or well that was washed, with the possibility that any contaminating material attached to its sides or inadvertently remaining in the container would interfere with the specificity or sensitivity of the assay. Additionally, the discarded liquids are often contaminated with hazardous material. Similar problems are encountered when the assay is done on a chromatographic paper strip.

In general, washing involves one of several methods: passage of wash solution over an immobilized material, repeated addition and removal steps to remove by dilution either in conjunction with centrifugation or immobilization with magnetic forces, or moving material into dense fluids of varying specific gravities or stabilized gel by centrifugation or magnetic force. Typically, when stabilized gels or dense fluids are used they are directionally below the reaction mixture. It would be desirable to have a method that would bring the washed material into a more convenient position, above the reaction mixture, for further manipulation and have a greater range of specific gravity for the wash fluid so that wash fluid of greater, similar or lower specific gravity could be used in the same method.

Unfortunately, many of the washing systems typically involve repeated flushing and resuspension, centrifugation and decanting steps which are laborious when performed manually and greatly complicate automated diagnostic instruments and make them more expensive.

Washing by lateral flow, flow-through and similar methods require slower, less effective and dilutive washing steps where liquid or wash solution is moved over an immobilized material in a single step or repeated addition, dilution, and removal steps. These methods are cumbersome, requiring large amounts of wash solution which need to be disposed of as a hazardous material, and typically rely on washing the sample in the original container previously contaminated by the heterogeneous sample or reaction mixture.

In some laboratory methods the material of interest is specifically captured on particles or microspheres as the solid state surface. Such particles or microspheres are employed in many and varied diagnostic and preparative methods. Their primary purpose in these methods is to separate or purify specific items of interest from unwanted surrounding contaminating materials. Similarly, in blood bank red cell testing, the red cell itself is the particle surface that captures material of interest. The active binding agents affixing such particles include antibodies, ligands, lectins, oligonucleotides and many other specific binding molecules of non-immune origin. Methods are well known and commonly practiced which enable the preparation of particles and microspheres of various size, specific gravity, and other properties to be attached to reagents which can specifically bind to specific cells, viruses and sub-cellular particles or other materials of interest.

When particles of various kinds are bound to materials of interest, they become much larger complexes which settle more rapidly under Stokes law. Larger denser complexes can be sedimented or centrifuged from a mixture and thus washed. Unfortunately this method requires centrifugation to create force to move the particles, and the medium must have a lower specific gravity than the particles which restricts the media that can be used and limits the power of the separation.

Some current separation methods use, as an alternative to centrifugation, separation by a process in which magnetic particles are bound specifically to the materials of interest to form a complex which is then selectively separated from materials not of interest by the pull of a magnetic field rather than by centrifugation or by gravity alone. Usually the material to be separated is pulled to the side of the vessel by magnetic force and the material not of interest removed by decanting or rinsing or other liquid flow past the material of interest held on the wall.

A current art-preferred method of conducting a wide variety of assays involves the use of individually coated chromatographic strips whereby a sample suspected of containing the analyte sought to be determined is applied either alone, or with appropriate reagents, to a chromatographic membrane or layers of membranes and allowed by lateral flow to come into contact on the strip with previously immobilized materials. Depending on the nature of reactants chosen, the immobilized reagents act to separate the desired test components so that a proper determination of the presence of the analyte can be made. This procedure typically passes the sample and labeled reagents laterally along a chromatographic strip and into the binding zone to bind with an immobilized reagent. Non-specific binding material to the immobilized reagent or to the strip is to be avoided or eliminated and therefore sufficient wash liquid must pass through the zone to remove unbound material. Flow-through procedures work in similar fashion, however the sample and labeled reagents "flow-through" immobilized reagents held in vertical proximity, rather than the horizontal proximity used in the chromatographic approach.

While, in general, lateral flow methods have the advantage of eliminating centrifugation steps and much of the liquid handling steps required for washing reactants in other methods, many lateral flow methods involve reagent addition steps during the procedure. For example, Becton Dickinson ColorPac® lateral flow devices may require pipetting of as many as six reagents during an analytic procedure.

An alternative chromatographic strip technology has been described in U.S. Pat. Nos. 6,713,271 and 6,136,549 to Christopher C. Feistel. In these two patents, magnetic assay methods and systems are described in which uniform bulk-prepared microparticle reagents and liquid reagents are substituted for the immobilized materials commonly used on the strip. Instead, magnetic particle-tagged reagents participating in the test and flowing on the strip are captured and held at a desired site on the strip by a magnet field applied to the site. The captured particles are read to determine the presence or absence of the analyte sought. Large volumes of wash liquid are required to move sample and unbound reactants away from the observation zone.

Density gradient separation is a commonly used separation method that employs a density gradient column and centrifugation. Density gradient separation methods separate materials of a mixture based upon their density. Materials of different density will spin down under centrifugation until they reach a liquid media layer of equal specific gravity. They "float" and do not enter the regions of density equal or higher than their own.

In pre-transfusion testing (PTT) of patients and donors, the gel method is a reliable method of choice, and utilizes a centrifuge method of washing red cells that relies on spinning the cells through a fluid zone of carefully chosen specific gravity such that the red blood cells (RBC), will spin down and contaminating proteins will be floated off. This method was first used in the Simwash technique developed by Graham et.al. in the 1980s. Excellent washing is accomplished but a narrow specific gravity range is required Separation based on the rate of sedimentation of particles through a density gradient to separate them from materials with a lower specific gravity that will either float on the density gradient or move to a different layer in the gradient or sediment at a slower rate than the larger particles has been used for blood bank serological testing. In this method, cells are forced by centrifugal force through a solution of intermediate density which allows the heavier red blood cells to pass through and floats the less dense serum on the top. The washed red cells can either be recovered following a decant step or be assayed in place by incorporation of a reagent into the solution of intermediate density, eliminating the need for a decant step.

Blood Banks collect more than 15 million units of blood annually for more than 14 million transfusions in the United States. Pretransfusion testing of patient and donor blood samples is an enormous industry distributed over nearly 10,000 large and small blood bank laboratories.

Blood Banks perform tests to determine the blood type of red blood cells of donors and patients, to detect antibodies in blood sera, and perform compatibility (crossmatch) tests and for potential infectious disease agents in every donor blood sample.

The following blood bank tests are among the most important and most frequently conducted tests:

Direct red cell antigen testing, typically ABO grouping and Rh typing

Reverse grouping (testing for antibodies in serum which react with A or B cells)

Antiglobulin based tests which require a serum protein removal step as a part of the procedure. These include indirect typing procedures for antigens (such as Kell, Duffy, Kidd and some Rh), direct antiglobulin test (test for serum proteins on an individuals' red cells), indirect antiglobulin tests (includes antibody screening, antibody identification and the crossmatch).

The following is a description of common blood bank reagents and techniques.

THE DIRECT COOMBS (Antiglobulin) TEST: The direct Coombs (antiglobulin) test is used to determine the in vivo bound incomplete antibody (IgG) bound to the red cells. It is also used in the investigation of anemias to demonstrate whether red blood cells are coated with incomplete antibody, including that of babies born to Rh-negative mothers. It will reveal whether antibodies have been adsorbed on the surface of the red cells while the baby was in the uterus and is important in diagnosing Rh hemolytic disease of the newborn. The direct Coombs (antiglobulin) test is performed by washing the red blood cells to be tested and attempting to agglutinate them with Coombs (antiglobulin) reagent. The Coombs reagent is widely available. This test, as well as the indirect test described below, are variously referred to herein as Coombs test, anti-globulin test, AHG test or variations thereof. The serum is variously referred to as Coombs serum, anti-human globulin serum, AHG serum or the like.

The antiglobulin test, associated with blood transfusion safety, is critically important and is the gold standard in pre-transfusion testing. The antiglobulin test detects whether red cell antibodies have reacted with red blood cells. Current test methods require careful washing of cells by multiple centrifugation steps before the test can be run and read. Because of concern for potential neutralization of Coombs serum, a reagent used for antiglobulin testing, much care in washing and agglutination reading skill is needed in manual antiglobulin method.

THE INDIRECT COOMBS (Antiglobulin) TEST: The indirect Coombs (antiglobulin) test is used to screen the patient's serum for atypical antibodies such as Rho (D), Kell (K), Duffy (Fya), and hr' (c) with known antigens. The presence of any of these atypical antibodies can cause hemolytic disease of the newborn or transfusion reactions.

In the indirect test, an unknown serum is tested with human group O reagent red blood cells. Group O reagent antibody screening cells are available commercially. They are a group of two or three O Rh positive and Rh negative donor red blood cells selected so as to be positive on at least 50% of the cells for each of the common clinically important red blood cell antigens. If a serum gives a positive reaction with such screening cells, tested separately or as a mixture, it must contain an atypical antibody of unknown identity. The techniques involved in performing the direct and indirect antiglobulin and the reasons therefor, are well-known in the art.

ABO GROUPING: Red cell (forward) typing with anti-A or anti-B reagents will demonstrate the presence or absence of A and B antigens on the red cell. Serum (reverse) typing with reagent A and B red cells will demonstrate the presence of anti-A and anti-B in the serum.

OTHER REAGENTS USEFUL IN ABO GROUPING: Other reagents may be used routinely in ABO grouping. They are often essential for resolving discrepancies between forward and reverse typing. Blood is not usually released from the blood bank for transfusion until any such discrepancies have been resolved. Anti-A, B (Group O serum) can detect weak A variants that may be missed by regular anti-A reagent. Other reagents include Anti-$A_1$ reagent (absorbed B serum or Dolichos lectin), Anti-H lectin (Ulex), Reagent O Rh-positive screening cells, Reagent $A_2$ cells and others.

COMPATIBILITY TESTING: Crossmatch (compatibility) tests are performed to determine the suitability of the donor's blood for the particular recipient. Blood transfusions are not given before performing a major crossmatch to test the donor's red cells against the serum of the recipient. If both donor and recipient are of the same blood group, a minor crossmatch may be done to test the recipient's red cells against the donor's serum. The minor crossmatch is of no value when donor and recipient belong to different blood groups because agglutination will occur. Major Crossmatch involves mixing donor's red cells with recipient's serum, incubating, centrifuging and adding antiglobulin reagent. Minor Crossmatch includes mixing donor's serum with recipient's red cells, incubating, centrifuging and adding antiglobulin reagent.

Rh TYPING: The crossmatch makes it possible to avoid hemolytic transfusion reactions following a particular transfusion. Blood banks are also concerned about isosensitization. If, for example, a blood bank selects Rho (D)-positive blood for an Rho (D)-negative woman, she will not have an incompatible crossmatch or a transfusion reaction if she has no anti-Rho (D) antibodies in her blood, but she may become sensitized to the Rho (D) antigen. Initiation of the immune response presents problems for subsequent transfusions and for subsequent pregnancies if she has an Rho (D)-positive mate. Rho (D) negative donors, Rho (D)-negative women and their Rho (D)-negative mates, and Rho (D)-negative cord bloods are tested for the presence of Rho\variant (DU) antigen that may not always be detected without the antiglobulin test. Various Rh typing methods and the appropriate controls are well-known to the art.

ANTIBODY TESTS: Screening for antibodies is especially important for patients receiving blood and the obstetrical patient. In obstetrical patients, early detection allows time to prepare for possible intrauterine or exchange transfusion in cases of Rh hemolytic disease of the newborn. Once the presence of an antibody has been detected, the problem of its identification remains, but this has been simplified by the development of antibody identification panels of group O reagent red cells. These screening and identification methods are well known to those skilled in the art.

Most blood bank tests require a wash step during the procedure. The centrifugal washing step, either by dilution and decant or sedimentation into beads or gel, takes about 5 to 10 minutes. The indirect antiglobulin test (IAT) is the most used and most reliable test in blood banking to determine binding of antibodies to red blood cells. This test is performed manually in test tube, requires addition of red cells and antisera, three manual centrifugation and decanting steps and finally a careful evaluation by a skilled technologist of whether the red cells have agglutinated, and recording of results. It is very labor intensive.

Although red cells in the presence of appropriate antibodies may clump in the absence of centrifugal forces, centrifugal procedures are typically used for almost all blood bank serological assays to cause enhanced aggregation of red cells for naked eye visualization at the assay end point. This is a major cause of a need to repeat an assay.

Classically, blood bank methods for determining blood types or detecting red cell antibodies in donor or patient sera are done manually in a large percentage of blood banks and rely upon hemagglutination as the endpoint to determining whether red cell antibodies have reacted with red blood cells in donor or patient blood samples.

Blood bank testing procedures have historically been a somewhat special case in the immunoassay art because the red blood cell, which is not visible to the naked eye, can form agglutinates that are visible to the naked eye and have a pattern distinguishable from that of nonaggregated red blood cells. Thus the typical blood bank procedure relies on human pattern recognition to detect a reaction. In blood bank testing, a wide variety of tests are performed using traditional, manual techniques that have been used for decades.

In recent years the manual DiaMed-ID (D-ID) antiglobulin gel test (Ortho Clinical Diagnostics, Raritan, N.J.) has largely replaced the classical manual method. It requires a ten minute centrifugation step and a more straightforward manual reading.

More and more testing is now being performed on automated instruments. For example, the Ortho Pro-vue (Ortho Clinical Diagnostics, Raritan, N.J.) is an automatic gel technology system, while the NEO and Galileo instruments (Immucor, Norcross, Ga., TANGO Optimo (Bio-Rad, Cressier-sur-Morat, Switzerland) and the Beckman PK7300 blood center instruments (Beckman Coulter, Brea, Calif.) are other large volume systems. The Immucor and Bio-Rad instruments require centrifugation while the Beckman instrument is not able to perform the antigolublin test.

BRIEF SUMMARY OF THE INVENTION

The invention provides a method for detecting a material of interest, usually an antibody or an antigen on a red blood cell, in a liquid by providing a novel method of detecting the antigen/antibody reaction. The invention is particularly suited for use in assay systems which involve the use of red blood cells, either as a reactant or as a sample, to determine unknown antibodies or blood group antigens. The following steps show a general scheme of the process of the invention. In step 1, the reaction mixture of the appropriate reagents is formed. For example, red cells in suspension are incubated with magnetic particles that will bind to red blood cells of all blood groups, and with serum that may contain red blood cell antibodies, or with red cell antibody reagents. The mixture is incubated and mixed at slightly elevated temperatures, e.g., from slightly above room temperature to about 37° C.

In step 2, the incubated reaction mixture is pipetted out and transferred to the capture vessel of the invention which contains a wash fluid, anti-human serum (if used), a paramagnetic element and a magnet.

The magnet is usually outside of the vessel, preferably below the vessel, and provides the magnetic field, preferably below the vessel.

In step 3, the reaction occurs between the reaction mixture and the AHS, if used. The magnet is energized and pulls all magnetic particles toward the paramagnetic element. Red blood cells with bound magnetic particles are forced down through the wash fluid by the magnetic field and washed free of all ambient or adherent human serum proteins which would neutralize the AHG reagent.

The magnetic red blood cells are attracted to and are deposited on the paramagnetic object forming a film or aggregates on the surface thereof. Red blood cells coated with antibody will be agglutinated and become firmly attached like a film onto the textured surface of the paramagnetic object. Red blood cells not coated will lie on the surface, not agglutinated (like sand), free to be resuspended.

In the next step, the magnetic field is removed and a vibratory disruptive force is applied to the paramagnetic element in the device. There results an adhering polymeric deposit or large agglutinates in the case of a positive result, or a cloud of free red blood cells, and paramagnetic particle micro aggregate complexes around the paramagnetic object in the case of a negative test. The negative and positive tests which can be read visually or by an optical pattern recognition system through the transparent bottom of the washing element vessel.

BRIEF SUMMARY OF THE INVENTION

More specifically, according to the invention, the reaction, when carried out in a specific manner, permits the observation of positive or negative reaction products in a novel way. The reaction scheme involves the use of magnetically tagged reagents in a reaction mixture which contains red blood cells and is suspected of containing the material of interest, to produce a magnetically tagged reaction product. In order to produce optimally useful magnetically tagged red blood cells, a significant number of red blood cells are reacted with a minimal number of magnetic particles to yield typically 2 or 3 red blood cells attached to each magnetic particle and having many unreacted red blood cells and virtually no unreacted magnetic particles. The magnetic product and magnetic starting materials are directed by magnetic propulsion to, and deposited on, a paramagnetic capture element or substrate in a capture vessel. The deposit on the substrate will exhibit different properties depending upon whether or not the antigen/antibody reaction has taken place. A deposit of the antigen/antibody reaction product adheres tenaciously to itself and the substrate while the deposit of any unreacted magnetically tagged material is weakly adhering. The integrity of the latter deposit is easily disrupted and dislodged under a disruptive force which would be insufficient to dislodge the reacted deposit. This difference in cohesive property provides the means by which a positive result is distinguished from a negative result.

An advantage of the method results from the fact that the magnetic propulsion step occurs in a wash fluid which will clean the reaction product, if one is formed, as it approaches the paramagnetic substrate. For some reactants, the wash fluid may also contain an extraneously added reactant which provides the means for enhancing the determination of positive versus negative results. That reactant is preferably an anti-species gammaglobulin, Coombs serum for example, (antihuman serum in human blood testing, AHS or AHG hereafter) or any other material which will react with an antibody. With the added presence of the AHG, a reaction mixture containing, for example, magnetically tagged red blood cells and a sample suspected of containing an antibody, will produce a magnetically tagged antigen/antibody complex (if the antibody is present) which will then react in the wash fluid with the extraneously added anti-species gammaglobulin. The resulting deposit will thus be a positive and will be tenaciously adhered to itself and to the paramagnetic capture element even after removal of the external magnetic field. In the absence of a cognate antibody in the reaction mixture, there will be no subsequent reaction of the extraneously added gammaglobulin with the magnetically tagged red blood cells, and therefore the negative product will be seen in various forms such as a weakly adhering deposit or after as a loose cloud-like dust or possibly a small particle on the bottom of the tube after removal of the external magnetic field.

If it is desired to determine whether a given antigen is present on a red blood cell, the sample RBC would be tagged with the appropriate magnetic particles and reacted with known antibody reagents. If desired, alternatively, the RBC unknown could first be reacted with a magnetically tagged material capable of reacting with RBCs, such as a tagged lectin or some other tagged universal RBC reactant.

For some reactions, i.e. those producing a direct agglutination using complete antibodies of the IgM type, the Coombs serum is not necessary to aid the visualization of the agglutination and in that sense the AHG is an optional reactant. The invention relies on the discovery that a magnetically tagged antigen/antibody complex alone or reacted with an anti-species gammaglobulin, when magnetically deposited on a paramagnetic element or substrate yields a robust, tenacious polymeric film which adheres strongly during application of the disruptive forces to the surface of the substrate and strongly to itself as a film or free agglutinates after the magnetic field is removed. It will also follow, adapt to and adopt the underlying structure, or latticework of the substrate. It is extremely difficult to remove such a deposit from a convoluted understructure. On the other hand, the bond between a tagged red blood cell and a non-specific binding agent with no antiglobulin to strengthen the bond, results in only a weak bond between the two which does not amount to the strength of an agglutination, and is easily dislodged from the underlying substrate on which it is deposited. An unreacted tagged red blood cell will likewise be easily disrupted. Thus, the firm adherence of the reaction product to the underlying structure or the formation of agglutinates is a sign of the occurrence of the antibody-antigen reaction, while an easily disrupted or dislodged deposit is evidence of the absence of the antibody-antigen reaction.

The subject invention accomplishes the separation and washing and determination of the presence of materials of interest, primarily antigens and antibodies, and most especially blood cell group antigens and serum antibodies, without numerous disadvantages of the prior art techniques. The magnetic propulsion through a clean liquid wash zone and deposition upon a paramagnetic substrate effects a cleaning action on the material of interest. The magnetically tagged materials are forced by the magnetic field into contact with the capture paramagnetic element present in the device, while the wash fluid remains essentially static as the particles to be examined are moved through the fluid and cleaned. The wash fluid provides an ideal environment for cells which can be maintained during the procedure. The novel method of the invention is also more flexible and less limited in potential application and enables efficiencies that centrifugal washing methods either cannot match or are difficult to achieve. The subject invention simplifies and improves the typical laboratory manual test methods utilized currently for detecting the reactions between cells and antibodies, or other ligand binders specific for antigens on the surface of the respective cells.

The capture device or vessel is a critical, central part of the invention and comprises a paramagnetic element, zone or moiety in a wash fluid. It is the vessel in which the reaction mixture, i.e. the reactants and reaction products, if any, are present and in which they interact with the capture paramagnetic element. The capture element is paramagnetic and capable, when magnetically energized, of binding all magnetic particles whether of interest or not. The device also either comprises or is associated with a source of a magnetic force.

As will be described in more detail below, for most blood banking tests, the magnetically tagged complex comprising the reaction product of a red blood cell and an antibody can be produced by reacting known reagents with the unknown materials of interest in the sample. In the case of crossmatch determinations, the donor's blood cells are treated with the patient's serum and any incompatibility will be apparent without knowing the identity of the specific antigens causing the problem.

When the material of interest is an antibody in a patient's blood, the reactants are usually magnetically tagged red blood cells comprising known blood group antigens and the patient's serum. A formed complex will be reactable with anti-human serum as previously described.

If the material of interest is an antigen on a red blood cell, then the sample would be patient's unknown RBCs. In such a case, the magnetic particles could be attached directly to the RBC sample, or if that were not desired, convenient or feasible, the unknown RBCs could be attached via an intermediate linking agent. That is, a magnetically tagged lectin or other universal red blood cell binding agent could be reacted with the RBC sample and thus provide the magnetically tagged RBC in that manner. All such reactants and reactions are fully known and understood by those skilled in the art.

In the view of the foregoing, the method and device of the invention can thus be described generally as:
1. A method for determining the presence of a material of interest in a sample, in which the material of interest is either,
   1 a) a blood group antigen present on a red blood cell, or
   b) an antibody that binds to a blood group antigen present on a red blood cell, which comprises treating the sample with a binding partner for the material of interest, the binding partner being an antibody which binds with the red blood cell group antigen of a) above or said binding partner of the material of interest being the blood group antigen present on a red blood cell in b) above, and wherein said red blood cells are either directly tagged with magnetic particles or indirectly tagged through a linkage to the red blood cell with a red blood cell binding agent such as a lectin tagged with magnetic particles,
2. Provide a capture vessel of the invention comprising a paramagnetic capture element, and a wash fluid which optionally comprises an anti-species globulin such as Coombs serum, either in the fluid or on the element or both.
3. Introduce the reaction product mixture of step one into the capture vessel of step.
4. Apply a magnetic force to the capture vessel whereby the capture element is rendered magnetic by said magnetic source, and the reacted Mag•MOI complex and any other Mag-tagged particles from the reaction mixture are moved into and through the wash fluid.

5. Allow the Mag-tagged materials to deposit on the capture paramagnetic element of the device and remove magnetic the field after deposition is complete.
6. Apply a disruptive force to the deposit to determine if the deposit is a strongly adhering deposit or large agglutinate, combined with or without AHS, or a weakly adhering negative blood cell antigen deposit.

The invention can utilize virtually any materials of interest which can be magnetically tagged in one way or another including cells, particles, nanoparticles and other materials, such as proteins, nucleic acids, viruses, bacteria and the like but is especially useful when the magnetically tagged reagent is a red blood cell and the materials of interest are serum antibodies.

Importantly, the invention simplifies nearly all such procedures and processes that require separation and purification of materials of interest from contaminating or interfering materials not of interest. Simplification comes largely from the elimination of centrifugation as a necessary step in the prior art and elimination of the need for fluid handling required for washing away contaminants, including reservoirs, pumps, tubing, valves and electronic controls that currently complicate instrument and equipment systems currently used in such procedures and processes.

The present invention is capable of performing virtually all tests that are performed in the blood bank which involve reactions between binding partners, such as antigen/antibody reactions and other immunological binding partners or universal binding partners such as lectins, biotin-avidin, Protein A or G, ligands and their receptors and the like. As so applied, magnets and magnetic particle-labeled reagents are used to capture and/or release magnetic particle-tagged entities for immunohematology diagnostic testing purposes. The magnetic particle tagged entities may be, depending on the particular assay, any of tagged antibodies, tagged blood cells, especially red blood cells, tagged universal binding partners, binding agents such as lectins, biotin-avidin, Protein A or G, ligands and their receptors and the like.

The invention is also amenable to automation and may employ software to sense the progress of the process to provide feedback to timing of incubation, reagent dispensing, order, amount of reagent dispensing, application of the disruptive force and initiation or removal of magnetic field and the like.

DETAILED DESCRIPTION OF THE INVENTION

The device and method of the present invention in a preferred embodiment, can be described as follows:

A reaction mixture of a sample to be tested, using the standard crossmatch test as an example, is provided. In this step, donor's red blood cells conjugated with magnetic particles, are contacted and incubated with patient's serum. If the patient's serum has antibodies to antigens on the tagged red blood cells, the red cells will be coated with patient's antibody. This mixture is also termed the "incubation mixture". The technology of this step is well-known in the art.

Next, a test device of the invention is provided. This device is preferably a tube type structure such as a well of a microliter plate tube filled with a suitable wash fluid of an appropriate specific gravity to prevent mixing with the reaction mixture and typically contains anti-human globulin (AHG) in addition the paramagnetic capture element. The AHG may also be present on the paramagnetic capture element, if desired. In the presently described embodiment, the assay is conducted in a microtiter plate well and the results of the reaction are read from the bottom of the well vertically through the tube axis. Another embodiment involves utilizing a well open at the bottom end. The properties of an open bottom device are selected so that the wash fluid is held in place against gravity by capillary action, surface tension or the like.

In any case, the wash fluid is suitably a buffer compatible with cells having an appropriate specific gravity. If the test is on non-human blood/serum it typically contains the appropriate anti-species globulin. Such materials are well-known in the art. The wash solution and anti-globulin reagent can be of a wide range of specific gravities from less than that of the incubation mixture to more than that of the incubation mixture depending on whether the motion of the reagents is upward or downward. The wash fluid may also contain reagents or growth media or other materials of benefit to later aspects of the procedure or objectives of the user.

The device is also provided with a paramagnetic capture element typically located near or on the internal bottom of the tube in the presently described, preferred embodiment. It could also be provided in the middle of the device, in the path of the subsequently moved tagged particles in the open tube embodiment. The paramagnetic element in the presence of a magnetic field becomes magnetized and attracts, and acts as a substrate for, the magnetically tagged particles moving through the device when the magnetic field is applied. The source of this magnetic field is positioned at the bottom of the tube so that the paramagnetic element is in the flow path of the downward moving mag-particles. The movement of the reacted and unreacted mag-tagged red blood cells is toward the magnetic source and therefore onto the paramagnetic object.

Following incubation of the magnetically tagged red blood cell suspension with patient serum in accordance with the usual procedure for conducting a major cross match, reaction mixture is transferred to the fluid-filled capture device tube and magnetic force applied from a source. The magnetic source may be below the capture device for the preferred embodiment and above it for the open tube version. The magnetic force causes a stream of movement of both the reacted and the unreacted magnetic particles downward in the reaction mixture, and through the wash fluid, there to be washed free of serum proteins. The anti-human globulin in this fluid reacts with any attached human antibody. The preferred way to practice the invention, as noted, is to conduct the process with the device in the upright or vertical configuration (instead of in a lateral or horizontal direction). In this way, the pull of the magnetic field is in the downward direction.

The magnetic source is positioned so that the paramagnetic object is in the stream of and between the moving tagged particles from the reaction mixture and the magnetic source. In the presence of the magnetic field, the paramagnetic element acts as a magnet to attract and localize the magnetic particle/red cells complex moving near it. During this phase, if the magnetically tagged red cells have reacted with an antibody, the complex thus formed will react with the AHG reagent as the complex moves through the wash fluid. The paramagnetic element which acts as a magnet will then become coated with the magnetic particle/red cell complex and attached anti-human serum and agglutination of the red blood cells will occur on the surface. In a major crossmatch, the materials of interest are any antibodies in the patient's serum which correspond to and are reactive with antigens on the red blood cell of the donor to form a complex. If there are such MOIs in the patient's serum, the complex will be bound by the anti-human serum which binds with human antibodies. The complex will thus be localized at the paramagnetic element. At this phase of the procedure, virtually all magnetic tagged materials utilized are deposited on the paramagnetic element and held there by the the magnetic field.

Once the complex has been deposited, the magnetic field is removed from the device and the component of adhesion of the deposit attributed to the field is correspondingly removed. While the complex is no longer held in place by the magnetic forces, it will retain its form until a disruptive force, a physical force of gravity or fluid flow for example, disassociates the deposit. Deposits containing the MOI are held together more firmly by the anti-human serum which binds the magnetic particle red cell immunoglobulin complexes together into a rubbery polymeric form, than the complexes that lack the MOI and the associated anti-human serum. More of this will be presented below.

Next, the magnetic force is removed and a disruptive force applied. Under these conditions, the presence of a deposit lacking the MOI will disassociate from the paramagnetic object more readily than a deposit with the MOI which will remain strongly cohesive and coated on the paramagnetic object. If the paramagnetic object is, as is preferred, a three dimensional object, instead of a simple planar surface, the complex will remain on the paramagnetic object even more tenaciously although there may be some agglutinates otherwise present. The surface of the paramagnetic object may be textured with protuberances, around which agglutinates will form, such that their release will be inhibited upon application of the disruptive force, yet allow unagglutinated free red blood cells to be readily dislodged. The retained presence of the magnetic particle-tagged red cell complex on the paramagnetic object or such agglutinates indicates a positive test and shows that the donor's RBCs are incompatible with the patient's serum. Agglutinates are large aggregates of the smaller paramagnetic microaggregates of the positive reaction.

If there were no red blood cell antigens present which reacted with the patient's serum, there would be no RBC/antibody complex formed and no binding of the anti-human serum. While the unreacted magnetic particles would accumulate on the paramagnetic object by reason of the magnetic tag, they would be dislodged by the disruptive force when the magnetic field is removed. This would signify a negative test and would confirm compatibility between donor's cells and patient's serum.

While the above discussion is directed to a cross match, virtually all immunohematology assays in which a red blood cell is reacted with an antibody to form an agglutinated clot, can be performed by this method and device. The invention provides a determination of whether or not immunoglobulin is bound to the red cell. The binding of immunoglobulin to red cells in all such assays occurs before the first complex is moved by a magnetic field into the device. This includes the "Direct Coombs" test where the binding has already occurred in vivo, in forward typing or grouping, in reverse typing, in testing for rare antigens on red cells, or in antibody screening, antibody identification, and major crossmatch, as well as the minor crossmatch. In some of the above assays, particularly forward and reverse typing, the immunoglobulin can often be detected without the need for addition of the antiglobulin reagent to the wash solution. Nevertheless, the presence of the antiglobulin reagent in the wash solution does not interfere and may assist with the assay in various ways.

This serological method provides several interesting differences from typical serological methods. First, the method collects only cells bound to magnetic particles (first complex and later complexes) onto the surfaces of a paramagnetic object creating new surfaces. Since that new surface is also paramagnetic, additional complexes become layered on to the coated surface in a repetitive process. Second, the cell magnetic particle complexes are concentrated by the method in a small space on the paramagnetic object and conform generally to the shape of the paramagnetic object. Third, the number of paramagnetic complexes needed to create an easily detected test result is less than expected because the complexes are concentrated on a surface and additional complexes will create more contact points for antigen/antibody interaction. This mass of complexes and potential antigens binding sites can be manipulated to maximize the sensitivity of the assay depending on the surface area of the paramagnetic object. Fourth, since few complexes are needed, disrupting them from the surface of the paramagnetic object would not create the significant turbidity or interference problem that has been observed with other test protocols and test method. Such turbidity may obscure the extent of the coating on the paramagnetic object after the positive result. Fifth, while the antiglobulin serum in the above discussion is used in a liquid state, it could also be immobilized on the surface of the paramagnetic object, providing another embodiment for attaching immunoglobulin-containing complexes to the paramagnetic object. Sixth, a variety of disruptive forces can be used, including gravity, ultrasound, agitation, vibration, fluid flow and many others. Seventh, although the preference embodiment described is to move the complexes downward, it is easy to design systems with the orientation in other directions where the complex is moved by magnetic force, washed, reacted with an antiglobulin reagent, coated on a paramagnetic object, exposed to disruptive forces and read. The paramagnetic object may also be an electromagnet that could be reversibly magnetized at will.

The serology of the immunohematological utility aspect of the invention may be generally stated as follows: First, mix in a container a sample of red blood cells and magnetic particles with an attached red cell binding agent that will react with these red cells or a sample of red blood cells that have already reacted with magnetic particles, and an antibody source or source of material that may contain antibodies, and/or a diluent. Second, incubate and mix the mixture as needed. Third, transfer the reaction mixture to the capture device tube and apply a magnetic field for the short period of time required to move them toward the paramagnetic object, to wash the complexes, to react them with an antiglobulin reagent, and obtain the attachment of the red blood cells tagged with magnetic particles to the paramagnetic object. Fourth, remove the magnetic field, or move the container and device away from the magnetic field. Finally, apply a disruptive force and read. It is apparent that these steps can be done at different stations that do not interfere with each other and lend themselves basically to automation.

The application of the disruptive force to free the unreacted tagged red blood cells from the paramagnetic element, will not be foreign to those skilled in the immunohemotology art since disruptive forces are commonly used in standard methods for observing reactions, clots or complex formations.

Technicians are often viewed tapping or snapping a finger against a test tube to dislodge or disrupt contents in aid of a reading. The use of a disruptive force in the present technique is one such force and will be easily employed by the art. In addition, in the automated assay field it is common to use equipment which can supply vibrations, shaking and the like, to the assay platform.

Moreover, it is also common in the art to perform positive and negative controls to aid in determining the end point of a reaction. Similarly in the present case, one may simply test the quantum of disruptive force needed to disrupt a negative deposit versus that of a tenaciously adhering positive deposit to determine the degree of positivity of the corresponding unknown, i.e. a one plus, two plus, three plus, etc.

While the inventors do not wish to be limited to any particular theory of operation in the present invention, it is felt that the integrity of the deposits on the paramagnetic element is a consequence of the bonding energies of the antigen/antibody reaction enhanced in some cases by the AHS reaction. Both the unreacted magnetically tagged RBCs and the magnetically tagged RBC/antibody/anti-antibody complexes, in the presence of a magnetic field, tend to link up separately with each other and deposit on the magnetized paramagnetic element. They will remain associated in that manner even in the absence of the magnetic field, until a disruptive force is applied.

The linkage of a positive reaction appears to form strong bonds that are surprisingly not easily disrupted. The deposits remain tightly bound to the paramagnetic element to which they were drawn when the magnet was energized.

The negative reaction product, of course, has only the unreacted tagged red blood cells or tagged red cells with non-specific binding agents deposited on the element. The absence of a cognate antibody and an immunoglobulin apparently imparts no intrinsic adhesive properties and the resulting deposits apparently simply disintegrate into a sandy type of loose covering or coating under slight forces once the magnetic pulling force is removed. This coating may appear in the tube as a cloudy dispersion around the paramagnetic element.

The present invention can be described as a method and device for separating and washing and determining the presence of or absence of materials of interest for materials not of interest in any reaction mixture comprising a complex of a red blood cell to an antibody to a red blood cell antigen, and an anti-antibody wherein the complex has a magnetic particle tag associated with it. It does not matter to the invention how the reaction mixture is prepared or how or where the complex is formed. For example, if it is desired to form the first complex (so called) between the red blood cell and the suspected antibody in an incubation step and then add the anti-antibody to that same reaction mixture, that would be an acceptable order. It is not preferred however, to follow that procedure. It is preferred to have the anti-antibody in a separate reaction in the capture device as will be described below.

The benefits of the invention are obtained from the use of the paramagnetic element as the substrate for the deposition of the formed complex of all three of the components namely the red blood cell, the cognate antibody, and the anti-antibody, under the influence of a magnetic field and the discovery of the difference in bonding cohesiveness between the formed complex components on the one hand and the lack of cohesiveness of unreacted reagents on the paramagnetic reagents on the other hand.

In that view of the matter, an embodiment of the invention can be described as starting with the appropriate reaction mixture (already reacted) and the capture device of the invention. In this description, the preferred method of having the antiglobulin present in the capture device is employed. Under these circumstances the captured device comprises a wash fluid and preferably an anti-antibody such as the Coombs Serum which is capable of binding with the antibody in the reaction mixture. Present in the capture device is the critical element of the invention namely, the paramagnetic object, which will act as the source of the attraction of the tagged complex aforementioned. The capture device as noted previously is a tube in the nature of a microtiter well, as is preferred in the invention or it can be an open ended tube which retains fluid by reason of surface tension and capillary action. But in this description, the device is preferably the well of a microtiter plate.

The reaction mixture from whatever source containing the components, whether reacted or not, is then introduced into the capture device, if it is not already present. The paramagnetic element is located preferably freely movable in the tube, but it may also be fixed or semi-fixed. It is preferred to be loose because in the subsequent magnetic activity it is desired to have the paramagnetic element move relative to the fluid in the tube. That is to say that the fluid may itself move around the paramagnetic element by shaking and such or it may move by the activity of the magnetic field pushing or pulling the device through the wash fluid.

Once the materials are in place the magnetic field is impressed on said device from the magnet which is located either below or above, preferably below, the tube and the purpose of which is to move the magnetic particles of the reaction mixture now in the capture device further into and through the wash fluid and into contact with the antiglobulin in the fluid or on the element as the case may be and ultimately into contact with the paramagnetic element. During this procedure the complex is washed free of materials that are not of interest and any three component reaction product namely a red blood cell/cognate antibody/anti-antibody complex binds to the element and attaches itself thereto under the influence of the magnetic field.

At this point, in order to determine whether or not the reaction is positive, that is whether a complex is formed or whether the starting reagent did not meet its cognate binding partner, the disruptive forces are applied to the complex and the resulting mixture submitted to the reading step. The reading step will determine whether the deposit on the paramagnetic element is a cohesive positive that remains and does not lose its integrity under the influence of the slight disruptive forces or whether it disassociates into the sandy, cloudy dispersion previously mentioned. The art is fully capable reading that condition. The liquid will either possess that cloudy look to it and that can be discerned or the deposit will appear as a fully developed cohesive coating on the paramagnetic element or as agglutinates.

The present invention is amenable to numerous embodiments via variations and combinations of reactants and conditions depending upon the nature of the assay being performed and the needs of the end user. As has been noted hereinabove, a major determination capability of the invention lies in its ability to detect the occurrence of an antibody/antigen reaction by detecting the presence of the antibody on a reaction complex and the treatment of that complex in a magnetic field environment. Accordingly, embodiments of the invention are possible varying the materials and conditions used in the formation of the complex and in the treatment thereof in the magnetic environment.

The following Table illustrates various blood bank tests which may be performed using the present invention.

TABLE OF GENERIC REACTIONS

| Test | Sample | Mag Labelled-Reactant |
| --- | --- | --- |
| 1. Major Crossmatch | 1. Patient Serum | 1. Donor Red Blood Cells |
| 2. Minor Crossmatch | 2. Donor Plasma/Serum | 2. Patient RBCs |
| 3. Antibody Screen | 3. Ab (Unknown) | 3. Reagent RBCs (Known Ag) |
| 4. Forward Typing | 4. Ab Reagent (Known) | 4. RBCs (Unknown Ag) |
| 5. Reverse Typing | 5. Serum (Unknown Ab) | 5. Reagent RBCs (Known Ag) |
| 6. Indirect Coombs | 6. Patient Serum | 6. Reagent Group O RBCs |
| 7. Direct Coombs | 7. Patient RBCs In Own Serum or Plasma | 7. Patient's RBCs |

Key:
Antigen = Ag
Antibody = Ab
Red Blood Cells = RBCs

The magnetic label may be introduced via direct reaction of magnetic particles with the RBCs or indirectly via magnet particles labeled with a red cell reactant such as a lectin or other universal red blood cell binding partner.

Evidence of reactions in the above occurs after the Sample and Mag Labeled Reactant are challenged with Coombs reagent (Anti-human globulin) in the capture device of the invention except for those tests which involve complete antibodies of the IgM type which generally do not need enhancement of agglutination visualization. Typical of such tests are forward and reverse grouping. Tests for antibody screening antibody identification, and crossmatch will all benefit from the use of AHG in enhancement of the visualization of the agglutinate.

The sample in the Direct Coombs test is the patient's RBCs which require no separate in vitro reactant since any adsorbed antibodies (the Material of Interest) on the RBCs would have been introduced in vivo prior to drawing of the sample. Washing of the cells occurs when the red blood cell-mag complex is pulled through the device of the invention through the wash solution.

The movable magnetic particle moieties preferred in the invention are magnetic particles available in the immunoassay art. Particles of various descriptions and sizes are widely available and the choice of the particular ones for use in a given assay depends upon the performance criteria of that assay. Usually particles in the 1-5 micron size are suitable. They are easily attached to the material to be tagged and techniques therefor are well-known to those skilled in the art. For example, they may be attached to the red cells by coating the magnetic particles with a red blood cell antibody to a red blood cell, or a lectin or other red blood cell binding materials.

The capture device comprises a wash fluid in the device. The usual wash solutions such as saline or the usual buffers used in the art are suitable taking into account the specific gravity depending on whether the magnetic force is in the upward or downward direction. When the device is open at the bottom such as provided by a pipette tip, the wash fluid should be capable, by capillary action, surface tension, vacuum and/or other forces, of holding the wash fluid in place against gravity. The physical characteristic of the fluids are selected to prevent undesired fluid movement out of the device. In this way, the device may be positioned above the reaction mixture. The wash solution can thus be of a wide range of specific gravities typically less than that of the reaction mixture. The wash fluid may also contain reagents or growth media or other materials of benefit to later aspects of the procedure or objectives of the user. The wash fluid may be water, saline or the usual biological buffers.

Reserved.

The washing step is extremely efficient in an unexpected and very short traversal distance through the clean wash fluid. Since only magnetically tagged materials will undergo propulsive movement under the magnetic force, any contaminating cells, proteins or other materials not of interest will be sheared off by the still fluid as the magnetic particles and the paramagnetic object are moved through the system relative to the still fluid. That this is the case that has been shown by the exceptional efficiency of centrifugal washing. In addition, if desired, automated equipment can be modified in appropriate cases to cause the fluid to move relative to the paramagnetic element and the mag-tagged particles to effect similar shear forces although this is not preferred.

Reserved.

The configuration, size and shape of the device and other physical properties are chosen to allow free migration of materials of interest under magnetic force yet prevent swirling or inappropriate premature mixing of fluids or reagents. The configuration can range from an open tube containing the liquid such as a pipette tip or a small open bottom microtiter well to one having a size, shape, dimensions and properties capable of holding entrapped wash fluid in place throughout the period of washing and manipulation of the device as needed in the procedure. The device may itself be an integral, unitary material of a variety of shapes and sizes. Suitable shapes are, cylindrical tubular shapes, flat or planar slabs and the like. Since test of the type described herein are done on a "micro" scale, such as with microtiter plates, the capture device is sized in a corresponding "micro" size.

The fixed or semi-fixed nature of the clean wash fluid in the capture device enables separation of clean materials from contaminated ones and stops convection, diffusion or other forms of fluid flow and neutralization of antiglobulin reagent by mixing with serum proteins. This is important in antiglobulin testing, for example, where mixing might inactivate the bound antiglobulin reagent and cause false negative test results.

The capture device of the invention includes a moveable or immobilized paramagnetic object. The purpose of this material is to act as a deposit site for all magnetic tagged particles which are exposed to the magnetic field source associated with the device. All magnetically tagged elements in the reaction mixture will be pulled to the paramagnetic object and be deposited there. Thus, this element must attract the magnetic-tagged particles when the field is energized. Use of a suitable magnet or other source of a magnetic field in close proximity to the paramagnetic device and the magnetically tagged materials in the capture device will ensure this.

A variety of shapes and forms of the paramagnetic element may be used. Such shapes as straight, curved or convoluted elements having adequate surface areas in light of the assay includes a ring, or group of rings, a sphere with protruding spikes, screens, scaffolding or a form of a twisted, bent, or contoured shape to provide a substrate to which the magnetic tagged reaction complex and by unreacted magnetically tagged reactants can conform. A spring shape is especially suitable since it can participate in the disruptive force application as well. Ring shapes, pretzel shapes and screens are preferred. It is important that the paramagnetic element be maintained at or near the bottom of the wash solution so that it will move in the fluid relative to the fluid when the vessel is vibrated, thus freeing unagglutinated red blood cells from the surface into a cloud. Preferably, the paramagnetic element is heavier or denser than the surrounding wash solution to keep it at or near the bottom of the solution. Another aspect of the paramagnetic element is that the surface may be textured with protuberances around which the red blood cell agglutinates form to inhibit dispersion of firmly agglutinated red blood cells from the paramagnetic element in positive tests.

The paramagnetic element is preferably freely moveable throughout the capture device and in such a case a preferred shape is a sphere with protruding spikes. When it is desired to have a semi-fixed element, a variety of other shapes may be employed especially a deformable type such as a coiled spring or a levered arm each anchored at one end, free on the other may be used since they may aid the application of the disruptive force. For example, when the magnetic field is applied, the tagged materials will move toward the deformable element which itself will move toward the magnet and be deposited on the element in the deformed stated. Removal of the field will result in the element returning to its original condition and in so doing would create the disruptive shearing force needed to dislodge a negative reaction product or be benign against the positive deposit.

For some applications, the capture element surface may be coated with anti-human globulin to bind red blood cells in a positive test, although it is preferred to have the AHG present in the wash fluid.

The capture device can be selected for transparency so that migration of the cells or materials of interest can be observed from the bottom, top or its sides and the rate and extent measured if required.

If the capture device is a tube configuration, it is possible to have an open void space at one or both ends held there by surface tension, but it is preferred to have the top end closed, except for a vent area. At the top, a zone would be available for functionally separated incubation steps or other processes, for timed adding of more reagents to the process.

As noted above, diagnostic test results can be read by simply applying the disruptive force to the deposited magtagged materials, eliminating the need for sophisticated image analysis of agglutination patterns. The preferred method of reading to distinguish positive tests from negative tests is to use optical pattern recognition software to read through the transparent bottom of each washing tube. The optical pattern of a positive test where the agglutinated red blood cells stick closely to the surface of the paramagnetic element after the disruptive force is applied, will be quite different from the optical pattern of a negative test where the red blood cells paramagnetic particle micro aggregate complexes will form a cloud around the paramagnetic element. Such discrimination is well within the capability of many of today's smartphone applications that read two dimensional barcode tags. If the tests were run in a 96 well microplate or in an 8 well array, a camera could picture all the wells at once, apply software pattern recognition to each well individually, and obtain a reading of all wells in less than one second. Such reading speed has great advantages in blood typing automation.

A major potential advantage of the invention for application to laboratory automation instrumentation is the elimination of the need for a centrifuge, thereby significantly reducing the extent and complexity of associated instrumentation modules and robotics to accomplish semi or complete automation

EXAMPLES

I. Attaching Microbeads to Red Cells to Make Paramagnetic Red Cell Microaggregates (PRCM):
Coating patient or donor red blood cells with paramagnetic particles coated with anti-rbc. In a well add 0.1 ml of anticoagulated whole blood and then add 0.1 ml of a suspension of the antibody to red blood cells coated paramagnetic particles containing 20,000,000 Dynabead particles. Mix to create microaggregates of red cells. Dilute with 0.8 ml saline and dispense to reaction vessels as required for assays below.

II. Five Reaction Vessels for Direct ABO Grouping, Rh Typing and Direct Coombs Test
  In five separate microtiter wells containing 50 microliters of the PRCM suspension from I above add:
  Forward grouping well #1—add 150 microliters anti-A Reagent
  Forward grouping well #2—add 150 microliters anti-B Reagent
  Forward grouping well #3—add 150 microliters anti-A,B Reagent
  Rh Typing well #4—add 150 microliters anti-D Reagent
  Direct Coombs well #5—add 150 microliters saline
  Mix by vibration and transfer immediately 100 microliters from each well to five separate paramagnetic object device vessels of the invention the first three containing wash solution with or without AHS and the $4^{th}$ and $5^{th}$ containing wash solution with AHS.

III. Three Reaction Vessels for Reverse Grouping with Reagent PRCM Suspensions of Group A Red Cell, Group B Red Cells, and Group O Red Cells
  In three separate microtiter wells containing 50 microliters of Reagent A, B, or O cell paramagnetic red cell microaggregate suspension add:
  Reverse grouping A Cell well #6—add 150 microliters of patient serum
  Reverse grouping B cell well #7—add 150 microliters of patient serum
  Reverse grouping O cell well #8—add 150 microliters of patient serum
  Mix by vibration and transfer immediately 100 microliters from each well to three separate paramagnetic object device vessels of the invention containing wash solution with or without AHS.

IV. Crossmatch with Donor Paramagnetic Red Cell Microaggregate or Reagent Group O Red Cell Microaggregate Suspensions
  In microtiter wells containing 50 microliters of the donor PRCM suspension prepared in I above or reagent group O PRCM suspension add:
  Crossmatch Donor #1 well—150 microliters of patient serum
  Crossmatch Donor #2 well—150 microliters of patient serum
  Antibody Screening #3 well—150 microliters of patient serum
  Mix by vibration, incubate at 37° C. while mixing and transfer 100 microliters from each well to three separate paramagnetic object device vessels of the invention containing wash solution with AHS.

V. Paramagnetic Object Device Vessel Containing Saline or AHS when the Paramagnetic Object is in a Pipette Tip.
  A pipette tip containing a paramagnetic object in a fixed position across the interior of the pipette tip (and positioned near and visible from a transparent viewing window) is filled with AHS (antisera diluted in 0.15 M NaCl and 1% Bovine Serum Albumin) so that the AHS fills the pipette to a level above the paramagnetic object is used to pipet 100 microliters of the reaction mixture of interest into the bottom of the pipette so that the reaction mixture is below the AHS wash solution and the paramagnetic object is well above the interface of the AHS solution and the reaction mixture. Apply a magnet to the top portion of the pipette above the solutions and paramagnetic object so that the paramagnetic red cell microaggregate suspension is pulled upward into and through the AHS solution and on to the paramagnetic object. When the paramagnetic red cell microaggregate suspension particles have migrated to the paramagnetic object and are coating a surface of the paramagnetic object the magnet is removed. The paramagnetic red cell microaggregate particles are observed for agglutination by creating fluid flow by the inward and outward motion of fluid within the pipette (keeping the paramagnetic object within the AHS solution). Observed agglutination of the paramagnetic microaggregate suspension particles is a positive result and indicates the presence of an MOI. No agglutination indicates the absence of an MOI and unreacted PRCM particles. Note: if only direct agglutination testing is required, the AHS may be replaced with saline (0.15 M NaCl and 1% Bovine Serum Albumin) and the test is performed and interpreted as described above.

VI. Paramagnetic Object Device Vessel Containing a Dense Wash Solution or AHS in a Dense Wash Solution and a Moveable Paramagnetic Object Sitting on the Bottom of the Well or Suspended Above the Bottom of the Well.

A microtiter well containing a movable paramagnetic object is suspended above or placed on the bottom of a well but within the AHS wash solution of a specific gravity such that the reaction mixture has a lower specific gravity than the AHS wash solution, and the reaction mixture will float on top, and the test will be conducted within a time so the free red cells will not settle into the view zone during the application of the magnet, removal of the magnet and vibration phase and read phase. The flat bottom of the vessel is a viewing window for observation of the test and results. Place 100 microliters of the reaction mixture of interest on top of the AHS wash solution, apply a magnet to the bottom of the vessel so that the paramagnetic red cell microaggregate suspension is pulled downward into and through the AHS solution and on to the paramagnetic object. When the paramagnetic red cell microaggregate suspension particles have migrated to the paramagnetic object and are coating a surface of the paramagnetic object, the magnet is removed and the well vibrated. The paramagnetic red cell microaggregate particles are observed for agglutination during and after vibration. Observed agglutination of the paramagnetic microaggregate suspension particles is a positive result and indicates the presence of an MOI, no agglutination indicates the absence of an MOI and unreacted PRCM particles. Note: if only direct agglutination testing is required, the AHS may be replaced with wash solution and the test performed and interpreted as described above.

What is claimed is:

1. A method for determining the presence of a material of interest (MOI) in a sample, in which the MOI is,
   a). a blood group antigen present on a red blood cell, in said sample, or
   b). an antibody in said sample that binds to a blood group antigen present on a red blood cell,
   which method comprises,
   A. preparing a reaction mixture of a) or b) with a binding partner for the MOI whose presence is sought to be determined, said, binding partner, in the case when the MOI is as described in a), being an antibody which binds with the red blood cell group antigen of a) above, or,
      in the case where the MOI is an antibody as described in b) above, said binding partner of the MOI being the blood group antigen present on a red blood cell as described in b) above, wherein said red blood cells are either directly tagged with magnetic particles or indirectly tagged through a linkage to the red blood cell with a red blood cell binding agent such as a lectin tagged with magnetic particles, whereby the magnetically tagged red blood cell particles react with the MOI if present to produce a reacted magnetic particle/MOI complex, or do not so react if the MOI is not present and remain as unreacted magnetically tagged red blood cell particles,
   B. providing a capture vessel comprising a paramagnetic capture element, and a wash fluid which optionally comprises an anti-species globulin such as Coombs serum, either in the fluid or on the element or both,
   C. introducing the reaction product mixture of step A into the capture vessel of step B,
   D. applying a magnetic force to the paramagnetic capture element whereby the paramagnetic capture element is rendered magnetic by said magnetic force, and the reacted magnetically tagged particles/MOI complex and any unreacted magnetically tagged red blood cell particles from the reaction mixture are moved into and through the wash fluid,
   E. allowing the magnetically tagged particles to form a deposit on the paramagnetic capture element and thereafter discontinuing application of the magnetic force after deposition occurs,
   F. applying a disruptive force to the deposit on the paramagnetic capture element to determine if the deposit is a strongly adhering deposit or large agglutinate, combined with or without anti-species globulin, thus indicating a positive result for the presence of the MOI, or a weakly adhering blood cell antigen deposit thus indicating a negative result for the presence of the MOI.

2. The method according to claim 1 wherein the material of interest is a). blood group antigen present on a red blood cell.

3. The method according to claim 1 wherein the material of interest is b) an antibody that binds to a blood group antigen present on a red blood cell.

4. The method of claim 1 wherein said red blood cells are directly tagged with magnetic particles.

5. The method of claim 1 wherein the wash fluid comprises an anti-species globulin.

6. The method according to claim 5 wherein the anti-species globulin is Coombs serum.

7. The method according to claim 1 wherein a major crossmatch is performed, the sample is patient serum and the magnetic particle red blood cells are from a donor.

8. The method of claim 1 wherein a minor crossmatch is performed, the sample is donor plasma or serum and the magnetic label reactant is patient red blood cells.

9. The method according to claim 1 wherein said method is for antibody screening wherein the sample comprises unknown antibodies and the magnetic labeled particle is reagent red blood cells of known antigens.

10. The method according to claim 1 wherein said method is for forward typing the sample is a reagent of known antibody and the magnetic labeled reagent is of red blood cells with unknown antigens.

11. The method of claim 1 wherein said method is for reverse typing the sample is serum with unknown antibody and the magnetic labeled particle is reagent red blood cells of known antigens.

12. The method according to claim 1 wherein the method is for performing an indirect Coombs, the sample is patient serum, the magnetic labeled particles are reagent group O red blood cells.

13. The method according to claim 1 wherein the method is for a direct Coombs test, the sample is patient's red blood cells in its own serum or plasma and the magnetic labeled particle is patient's red blood cells.

14. The method of claim 1 wherein the paramagnetic capture element has anti-human globulin deposited thereon.

15. The method of claim 1 wherein the wash fluid comprises anti-human globulin.

16. The method of claim 1 wherein the paramagnetic element is fixed in the capture vessel.

17. The method of claim 1 wherein the paramagnetic element is freely movable in the capture vessel.

18. The method of claim 1 wherein the paramagnetic element is semi-fixed in the capture vessel and comprises a movable portion.

19. The method of claim 1 wherein the magnetic pull is in a downward direction.

20. The method of claim 1 wherein the paramagnetic element is of spherical shape and comprises protuberances thereon.

* * * * *